US00PP26037P3

(12) United States Plant Patent
Lee

(10) Patent No.: US PP26,037 P3
(45) Date of Patent: Nov. 3, 2015

(54) ***RHODODENDRON* PLANT NAMED 'HOMLEA'**

(50) Latin Name: ***Rhododendron* hybrid**
Varietal Denomination: HOMLEA

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 178 days.

(21) Appl. No.: 13/998,430

(22) Filed: Oct. 30, 2013

(65) Prior Publication Data

US 2015/0121582 P1 Apr. 30, 2015

(51) Int. Cl.
*A01H 5/02* (2006.01)

(52) U.S. Cl.
USPC ..... Plt./238

(58) Field of Classification Search
USPC ..... Plt./238
See application file for complete search history.

*Primary Examiner* — Anne Grunberg
(74) *Attorney, Agent, or Firm* — Cassandra Bright

(57) ABSTRACT

A new and distinct *Rhododendron* cultivar named 'HOMLEA' is disclosed, characterized by large white flowers, and a distinctive upright, narrow plants. Plants bloom Spring, Summer and Fall and maintain a low mature height. The new cultivar is a *Rhododendron,* suitable for ornamental garden purposes.

1 Drawing Sheet

Latin name of the genus and species: *Rhododendron* hybrid.

Variety denomination: 'HOMLEA'.

BACKGROUND OF THE INVENTION

The new cultivar is a product of a planned breeding program by the inventor, Robert Edward Lee. The inventor's intention was to develop compact growing *Rhododendron* hybrid plants with re-blooming characteristics. This new variety, hereinafter referred to as 'HOMLEA', was discovered as a seedling, resulting from the crossing of *Rhododendron* 'Watchet', unpatented with the pollen parent *Rhododendron* 'Conleb' U.S. Plant Pat. No. 10,581. The cross was performed during 1996, and the new variety selected during Fall of 2002 in Independence, La.

After identifying the new variety as a potentially interesting selection, the inventor first organized propagation of 'HOMLEA' by vegetative cuttings during the Fall of 2002 at a commercial nursery in Independence, La. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'HOMLEA' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HOMLEA' These characteristics in combination distinguish 'HOMLEA' as a new and distinct *Rhododendron* cultivar:

1. Unique Spring, Summer, and Fall blooming.
2. Clear white flowers.
3. Easily propagated with semi-hardwood cuttings in late Spring through the Summer.
4. Good specimen plant.
5. Good container plant.
6. Very good foundation plant.
7. Vigorous growth under normal fertilization and moisture conditions.
8. Hardy to Zone 7.
9. Attracts butterflies.
10. Unique upright growth.
11. Branches grow at acute angles.
12. Large, single flowers.

COMPARISON TO PARENT VARIETY

'HOMLEA' is similar in most horticultural characteristics to the parent variety *Rhododendron* hybrid 'Watchet'. Plants of the new cultivar 'HOMLEA' however, produce flowers that are white in coloration, compared to the pale pink flowers of the seed parent variety. Additionally, plant habit of 'HOMLEA' is overall more upright and less compact than 'Watchet'.

'HOMLEA' is similar in most horticultural characteristics to the parent variety *Rhododendron* hybrid 'CONLEB'. Plants of the new cultivar 'HOMLEA' however, produce flowers that are white in coloration, compared to the red flowers of the pollen parent variety. Additionally, plant habit is overall more upright and narrower in the new variety than the pollen parent.

COMMERCIAL COMPARISON

'HOMLEA' can be compared to the commercial variety *Rhododendron* hybrid 'Mootum' U.S. Plant Pat. No. 18,416. Plants of the new cultivar 'HOMLEA' are similar to plants of 'Mootum' in most horticultural characteristics, however, plants of the new cultivar 'HOMLEA' are significantly smaller at a mature age, and form a more upright, less spreading plant than 'Mootum'. Flowers of the new variety are single, whereas flowers of 'Moontum' are semi-double.

BRIEF DESCRIPTION OF THE PHOTOGRAPH

The accompanying photograph in FIG. 1 illustrates in full color a close up of typical flowers of the new variety.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'HOMLEA' plants grown outdoors in Loxley, Ala. Plants are approximately 3 years old, in a 3 gallon nursery container. Measurements and numerical values represent averages of typical plant types.

Botanical classification: *Rhododendron* hybrid 'HOMLEA'.

PROPAGATION

Typically by semi-hardwood cuttings in Spring and Summer.

Root description: Fine, fibrous young roots, well branched. Colored near RHS Grey-Brown 199A.

PLANT

Growth habit: Compact globular shrub.

Height: Approximately 50 cm to top of foliar and flowering plane.

Plant spread: Approximately 38 cm.

Branching characteristics: Well branched, approximately 8 primary branches from the center of the plant. Branches occur at acute angles, forming a very upright, dense plant. Angle of primary branches approximately 15° from center of plant. Each primary branches has 4 to 10 lateral branches.

*Primary branches.*—Length of Primary Branches: Average 25 cm. Diameter of Primary Branches: Approximately 0.6 cm. Primary Branch Strength: Very strong, difficult to break. Primary Branch Color: Near RHS Yellow-Green 152D, with age, covered with a thin bark like layer colored near Grey-Brown N199D. Primary Branch texture: Young growth hirsute, hairs, approximately 0.15 cm long, colored near Yellow-Green 151B. Older growth scaly, hirsute. Hairs colored near White 155D.

*Lateral branches.*—Number of Lateral Branches: Approximately 4 to 10 per primary branch. Length of Lateral Branches: Average 12 cm. Diameter of Lateral Branches: Average 0.35 cm. Lateral Branch Strength: Very strong, flexible. Lateral Branch Color: Near RHS Yellow-Green 152D. Lateral Branch texture: Hirsute. Internode length: Range between 0.8 to 3.0 cm. Age of Plant Described: Approximately 2 years.

FOLIAGE

Leaf:

*Type.*—Simple.

*Arrangement.*—Alternate.

*Average length.*—Approximately 3.8 cm.

*Average width.*—Approximately 1.7 cm.

*Shape of blade.*—Oblanceolate.

*Apex.*—Acute.

*Base.*—Broad attenuate.

*Attachment.*—Blunt.

*Margin.*—Entire.

*Texture of top surface.*—Pubescent. Hairs appressed.

*Texture of bottom surface.*—Pubescent. More hairs present along main vein and margin.

*Foliage scent.*—None.

*Color.*—Young foliage upper side: Near RHS Green 137B. Young foliage under side: Near RHS Green 138A. Mature foliage upper side: Near RHS Green 137A. Mature foliage under side: Near RHS Green 138A.

Venation:

*Type.*—Pinnate.

*Venation color upper side.*—Near RHS Yellow-Green N144A.

*Venation color under side.*—Near RHS Greyed-Orange 176C.

Petiole:

*Length.*—About 1.1 cm.

*Diameter.*—About 0.25 cm.

*Color.*—Upper Surface: Near RHS Yellow-Green N144C, Lower Surface: Near RHS Greyed-Orange 164B.

FLOWER

Bloom period: Plants flower in the Spring, then begin intermittent flowering cycles in late Spring/Summer through Fall.

Flower:

*Arrangement.*—Axillary clusters of perfect, open funnel shaped individual flowers. Typically 4 to 10 flowers per cluster.

Inflorescence:

*Height.*—Average 10.0 cm.

*Diameter.*—Average 11.0 cm.

Peduncle:

*Length.*—Average 1.7 cm.

*Diameter.*—0.3 cm.

*Color.*—Near RHS Yellow-Green 152D.

*Texture.*—Densely pubescent.

*Aspect.*—Straight to very slightly curved. Angle of attachment, approximately 15° angle from stem.

Flowers:

*Length.*—Average 5.0 cm.

*Diameter.*—Average 7.5 cm.

*Facing direction.*—Outwardly and upwardly facing.

*Persistent or self-cleaning.*—Petals self cleaning.

*Fragrance.*—None.

Tube:

*Tube length.*—Approximately 2.0 cm.

*Tube width a widest point.*—Approximately 2.1 cm.

*Tube width and narrowest point.*—Approximately 1.1 cm.

Petals:

*Unfused petal segments.*—

*Length.*—Approximately 3.0 cm.

*Width.*—Approximately 3.1 cm.

*Apex.*—Retuse.

*Shape of petal.*—Unfused portion, obovate.

*Petal margin.*—Entire. Ruffled aspect along margin.

*Petal arrangement.*—Approximately ⅓ fused from base.

*Petal number.*—5.

*Petal texture.*—Smooth.

*Color.*—Upper surface at first opening: Near RHS White 155A. Under surface at first opening: Near RHS White 155A. Inner surface at maturity: Near RHS White N155A. Outer surface at maturity: Near RHS White N155A. Upper surface at fading: Near RHS White 155A. Under surface at fading: Near RHS White 155A.

Bud:

*Shape.*—Elliptic.

*Length.*—2.9 cm.

*Diameter.*—1.1 cm.

*Color.*—Near RHS White 155A.

Calyx/sepals:

*Quantity per flower.*—5 sepals.

*Shape.*—Narrow deltate.

*Length.*—0.9 cm.

*Width.*—0.3 cm.

*Apex.*—Acute.

*Base.*—Fused.

*Margin.*—Entire.

*Texture.*—Highly pubescent.

*Color.*—Inner Surface: Near RHS Yellow-Green 144A. Outer Surface: Near RHS Yellow-Green 144B.

REPRODUCTIVE ORGANS

Stamens:

*Number.*—10.

*Length.*—3.5 cm.

*Width.*—0.1 cm.

*Color.*—Near RHS Green-White N157D, base Green 142C.

*Anthers.*—Length: Approximately 0.3 cm. Color: Near RHS Yellow-Green 145C. Pollen: Not observed to date.

Pistil:

*Number.*—1.

*Length.*—5.1 cm.

*Style.*—Length: 4.7 cm. Color: Near RHS Green-White 157C.

*Stigma.*—Globular, colored near Yellow-Green 145B.

*Ovary.*—Sericeous texture. Approximately 0.3 cm in diameter. Colored near Yellow-Green 145A. Hairs colored near White 155A.

OTHER CHARACTERISTICS

Disease and pest resistance: Not observed to be susceptible nor resistant to normal diseases and pests of *Rhododendron* hybrid.

Temperature tolerance: USDA Zone 6.

Fruit/seed production: Not observed to date.

What is claimed is:

1. A new and distinct cultivar of *Rhododendron* plant named 'HOMLEA' as herein illustrated and described.

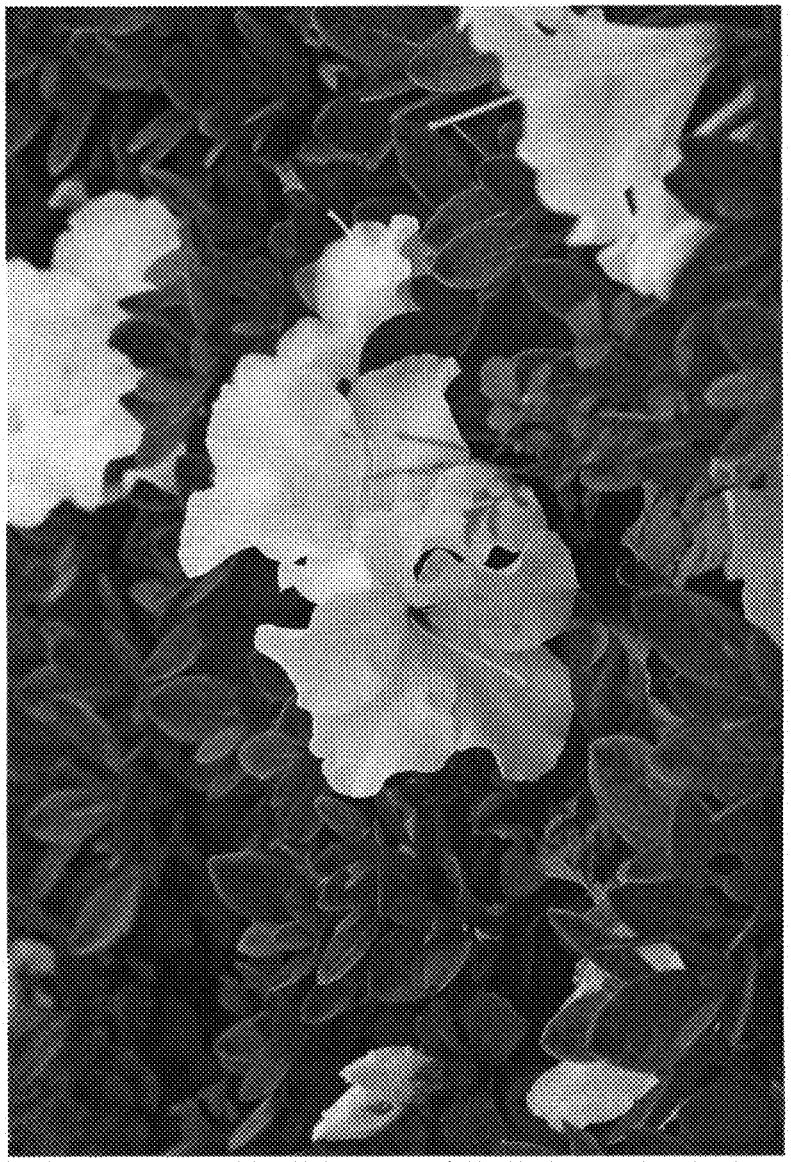

* * * * *